United States Patent [19]

Takahashi et al.

[11] Patent Number: 4,991,564
[45] Date of Patent: Feb. 12, 1991

[54] SHEATH DEVICE FOR ENDOSCOPE

[75] Inventors: Nagashige Takahashi; Teruo Ouchi, both of Tokyo, Japan

[73] Assignee: Asahi Kogaku Kogyo Kabushiki Kaisha, Tokyo, Japan

[21] Appl. No.: 547,054

[22] Filed: Jul. 2, 1990

[30] Foreign Application Priority Data

Jul. 4, 1989 [JP] Japan .................. 1-172698

[51] Int. Cl.⁵ .............................................. A61B 1/00
[52] U.S. Cl. ...................................................... 128/4
[58] Field of Search ........................................ 128/4, 6

[56] References Cited

U.S. PATENT DOCUMENTS

| | | |
|---|---|---|
| 4,646,722 | 3/1987 | Silverstein et al. ............ 128/4 |
| 4,721,097 | 1/1988 | D'Amelio ...................... 128/4 |
| 4,741,326 | 5/1988 | Sidall et al. ................... 128/4 |
| 4,771,766 | 9/1988 | Aoshiro et al. ............... 128/4 |
| 4,807,593 | 2/1989 | Ito ................................ 128/4 |
| 4,809,678 | 3/1989 | Klein ............................. 128/4 |
| 4,815,450 | 3/1989 | Patel ........................... 128/4 X |
| 4,869,238 | 9/1989 | Opie ............................. 128/6 |
| 4,878,485 | 11/1989 | Adair ......................... 128/4 X |

Primary Examiner—William H. Grieb
Attorney, Agent, or Firm—Sandler, Greenblum & Bernstein

[57] ABSTRACT

A sheath device for an endoscope comprises a sheath which is inflatable with a gas that is pumped into the inside of the sheath to allow an insert tube of the endoscope to be covered. A sheath cover, formed in the shape of a tube, surrounds the sheath with a space left therebetween to control overinflation of the sheath. A portion of the sheath cover, that surrounds the distal end portion of the sheath, is tapered toward the distal end of the sheath cover. A gas supply passage is provided for supplying a gas into the sheath to inflate it, and a gas pressure control device is provided with a bleeder which communicates with the gas supply passage and opens upwardly to the atmosphere. A ball valve is placed on the bleeder from the upper side thereof to close it.

13 Claims, 5 Drawing Sheets

SHEATH DEVICE FOR ENDOSCOPE

BACKGROUND OF THE INVENTION

1. Field of the Invention

The present invention relates to a sheath device for an endoscope, which is fitted over an insert tube of the endoscope when used for an endoscopic procedure and which can be removed and disposed of after use, to prevent the transmission of bacteria or viruses from one patient to another through the endoscope.

More particularly, the present invention relates to a sheath device for an endoscope, wherein a sheath, which comprises the device, is inflated with air so that the insert tube of the endoscope is smoothly inserted into and removed from the sheath which is in an inflated state.

This type of sheath device is provided with a sheath cover as being an auxiliary member which allows the sheath to inflate to a configuration that is the most suitable for insertion and removal of the insert tube of the endoscope, and which also prevents bursting of the sheath due to overinflation. This sheath cover also serves to isolate the sheath from the external environment when the sheath, which is contaminated during an endoscopic procedure, is drawn out of a hollow organ of the patient's body.

2. Description of the Prior Art

In the conventional sheath device for an endoscope, as shown in FIG. 5A, a sheath cover 101 is formed from a straight cylindrical member that has a uniform inner diameter, and it is designed to allow a sheath 102 to inflate until the outer diameter of the sheath 102 becomes equal to the inner diameter of the sheath cover 101. Air that is used to inflate the sheath 102 is sent into the sheath 102 through an air supply tube (not shown) that is connected to an external air supply pump.

However, since the sheath cover 101 has a uniform inner diameter, when the sheath 102 is inflated inside the sheath cover 101, it inflates radially and also expands along the longitudinal axis. In consequence, when the sheath 102 comes into contact with the sheath cover 101, an extra portion of the sheath 102, which expands in the longitudinal direction, is curled at the distal end of the sheath 102, as shown in FIG. 5B.

As the air is released from the sheath 102 after the supply of air into the sheath 102 has been suspended, the diameter of the sheath 102 decreases. In consequence, the sheath 102 is fitted over the insert tube of the endoscope with the curled portion being left as it is, as shown in FIG. 5C. In such a case, the endoscope cannot be used for an endoscopic procedure in a hollow organ of the patient's body.

In addition, since the amount and pressure of air that are needed to inflate the sheath depend on the type of sheath device employed, it is very difficult to control the air pressure with accuracy in accordance with each individual type of sheath device If the air pressure cannot effectively be controlled, the sheath may burst due to the oversupply of air. If the sheath or the sheath cover bursts when the sheath is removed after an endoscopic procedure, there is a danger of infection with pathogens which are scattered around from the endoscope.

SUMMARY OF THE INVENTION

An object of the present invention is to provide a sheath device for an endoscope, which is designed so that the sheath can be fitted over and removed from the insert tube of the endoscope in favorable conditions without the fear of abnormal deformation or bursting of the sheath.

Other objects and advantages of the present invention will become apparent from the following detailed description of an illustrated embodiment of the invention.

According to the present invention, there is provided a sheath device for an endoscope comprising: a sheath which is inflatable with a gas that is sent into the inside thereof to cover an insert tube of the endoscope; and a sheath cover which is formed in the shape of a tube that surrounds the sheath with a space left therebetween to control overinflation of the sheath, a portion of the sheath cover that surrounds the distal end portion of the sheath being tapered toward the distal end of the sheath cover.

In addition, there is provided a sheath device for an endoscope comprising: a sheath which is inflatable with a gas that is sent into the inside thereof to cover an insert tube of the endoscope; a gas supply device for supplying a gas into the sheath to inflate it; and a gas pressure control device for adjusting a pressure of the gas supplied by the supplying device at a predetermined level.

In addition, there is provided a sheath device for an endoscope comprising: a sheath which is inflatable with a gas that is sent into the inside thereof to cover an insert tube of the endoscope; a sheath cover which is detachably provided with respect to the sheath to control overinflation of the sheath, the sheath cover surrounding the sheath with a space left therebetween; and a gas supply tube connecting device which is provided on the sheath cover to connect a gas supply tube for supplying a gas into the sheath.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

Figure 1:
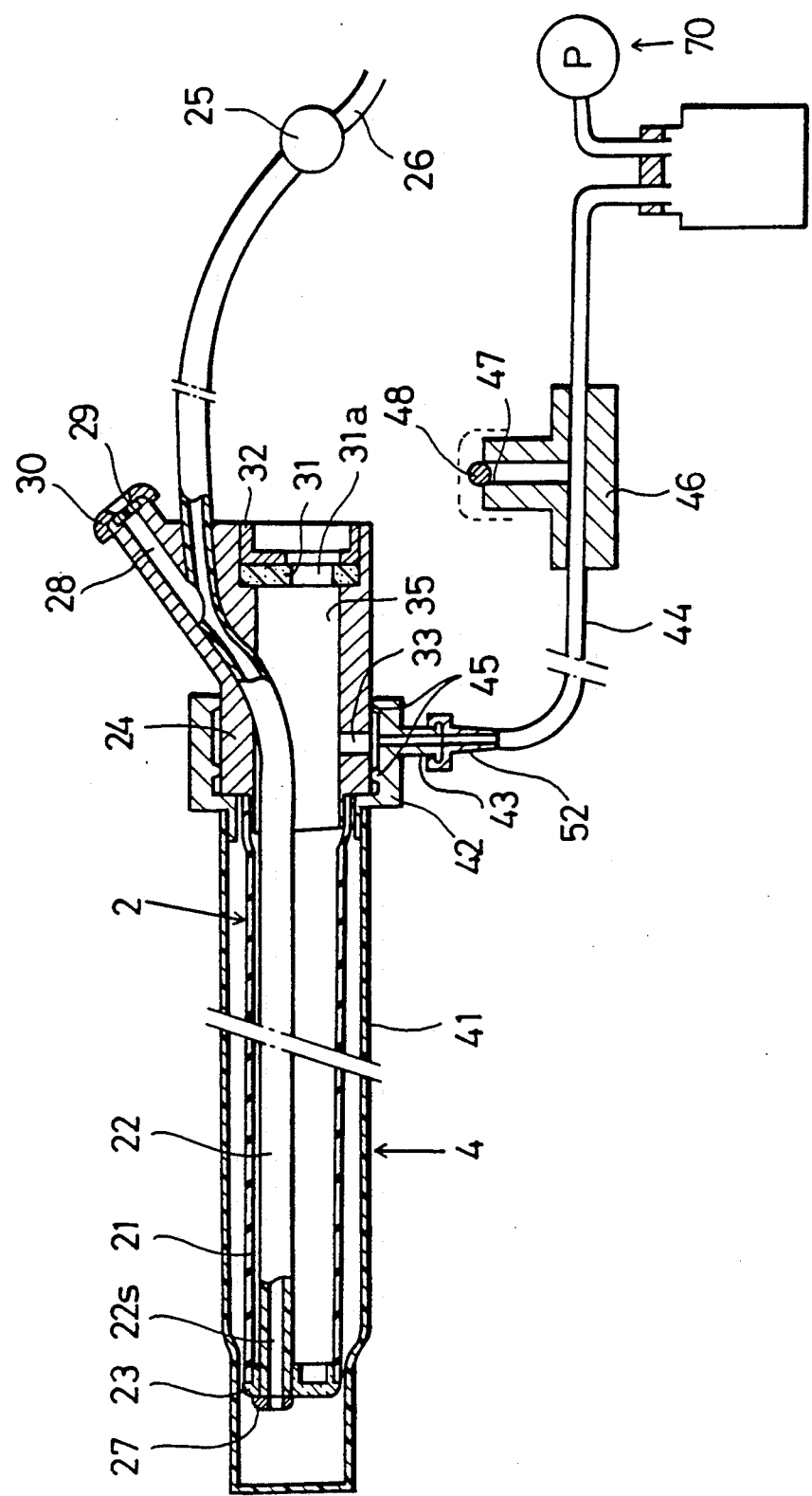
FIG. 1 is a sectional side view of the sheath device to be fitted over an endoscope of the present invention.
Figure 2:
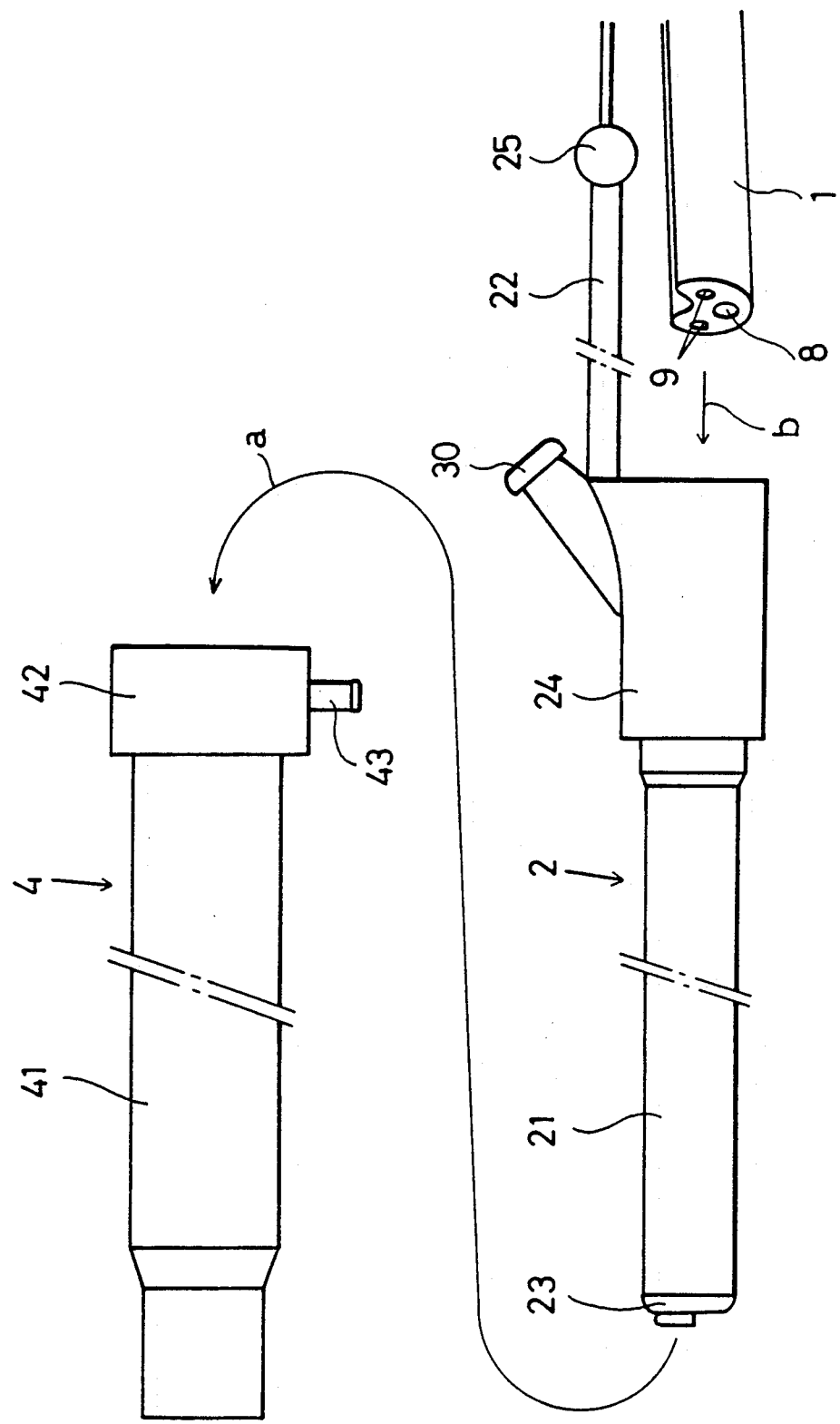
FIG. 2 is a perspective view of the sheath device for an endoscope according to the present invention.

FIG. 2 shows the external appearance of one embodiment of the sheath device for an endoscope according to the present invention, and FIG. 1 is a sectional side view of a sheath 2 which is inserted in a sheath cover 4.

In FIG. 2, reference numeral 1 denotes an insert tube of an endoscope, 8 a viewing window, and 9 illuminating windows.

Referring to FIGS. 1 and 2, the sheath 2 is removably fitted over the insert tube 1 of the endoscope to isolate it from the external environment. The sheath 2 comprises a tubular portion 21, a channel portion 22, a distal end portion 23 and a mouth portion 24.

The tubular portion 21 is formed in the shape of a thin-walled cylinder using an elastic material, for example, silicone rubber, and the distal end portion 23, which is formed from a non elastic, transparent material, for example, a transparent styrol resin material, is secured to the distal end of the tubular portion 21 in such a manner that no air leaks out from the sheath 2. The rear end of the tubular portion 21 is firmly bonded to the distal end of the mouth portion 24 in such a manner that no air leaks out from the sheath 2.

The channel portion 22, which is made of, for example, tetrafluoroethylene resin, includes a suction channel 22s which also serves as a forceps channel. Air and water supply channels are not shown.

The channel portion 22 extends through the sheath 2 over the entire length thereof. The rear end portion of the channel portion 22 extends from the rear end of the mouth portion 24, and a channel connector 25 is connected to the end of the channel portion 22. Thus, the channel portion 22 can be connected to a control mechanism (not shown) in the endoscope through the connector 25. Reference numeral 26 denotes a suction channel tube that extends from the channel connector 25 and is connected to an external suction pump (not shown).

The distal end portion 23 is formed with such a size that the distal end portion of the endoscope is loosely fitted therein. A nozzle piece 27 projects from the end face of the distal end portion 23. The nozzle piece 27 enables each channel in the channel portion 22 to open outwardly.

The mouth portion 24 is provided with a forceps inserting bore 28 which communicates with the suction channel 22s, so that a tool for an endoscopic procedure, for example, a forceps, can be inserted into the suction channel 22s from the forceps inserting bore 28. Reference numeral 29 denotes a forceps stopper, which is made of, for example, rubber, for passing a forceps or other similar tool in such a manner that no air will leak out, the forceps stopper 29 having, for example, shaped-slit that is formed in the center thereof. A cap 30 is attached to the mouth portion 24 to hold the forceps stopper 29.

Reference numeral 35 denotes an endoscope inserting passage for inserting the insert tube 1 (FIG. 2) of the endoscope. The bore 35 extends through the mouth portion 24 in substantially coaxial relation to the tubular portion 21.

A packing 31 is provided in an inlet portion of the endscope inserting passage 35. The packing 31 is formed from an airproof, flexible and elastic material, for example, expanded sponge that has a large number of minute closed cells, or silicon rubber. The packing 31 has a bore 31a which has the same cross-sectional configuration as that of the insert tube 1 (FIG. 2) and a slightly smaller size than the cross-sectional size of the insert tube 1. Thus, the packing 31 can hermetically seal the outer periphery of the insert tube 1 when inserted, without any gap. A packing gland 32 is provided with a bore which has a slightly larger size than the cross-sectional size of the insert tube 1.

An air supply opening 33 is bored in an outer wall portion of the mouth portion 24 so as to communicate with the endoscope inserting passage 35 to send air into the sheath 2.

The sheath cover 4 is removably provided for the sheath 2 in such a manner as to surround the tubular portion 21 of the sheath 2 with a space left therebetween, thereby preventing overinflation of the tubular portion 21. The sheath cover 4 comprises a tubular sheath cover member 41 and a sheath cover support member 42.

The tubular sheath cover member 41 is sufficiently strong to resist the inflating force of the tubular portion 21 of the sheath 2 and is formed in the shape of a tube, the distal end of which is sealed. Accordingly, filth, such as mucus or mucous membrane, will not leak out after the use of the endoscope.

A portion of the tubular sheath cover member 41, which is located around the distal end of the tubular portion 21 of the sheath 2 when the tubular sheath cover member 41 is set at a predetermined position where it completely surrounds the tubular portion 21 i.e., at a position where the sheath 2 is fully inserted into the sheath cover 4 is inwardly tapered toward the distal end. A relatively short portion of the tubular sheath cover member 41, which is closer to the distal end than the tapered portion, is formed with such an inner diameter that the distal end portion 23 of the sheath 2 is loosely fitted therein, whereas a relatively long portion of the tubular sheath cover member 41, which is closer to the proximal end than the tapered portion, is formed with an inner diameter which enables the insert part 1 of the endoscope to be loosely inserted and removed and which is smaller than a critical diameter at which the tubular portion 21 bursts from overinflation.

The sheath cover support member 42 is bonded to the proximal end portion of the tubular sheath cover member 41. The mouth portion 24 of the sheath 2 is fitted to the support member 42. Reference numeral 43 denotes an air supply nipple for connecting an air supply tube 44 that may be connected to an air supply pump 70. The air supply nipple 43 communicates with the air supply opening 33 in the mouth portion 24 of the sheath 2. Seal portions 45 project from the inner surface of the sheath cover support member 42 so as to come into close contact with the outer peripheral surface of the mouth portion 24 of the sheath 2, thereby sealing the sheath 2. It should be noted that a mouthpiece 52 of so-called lure-lock type is attached to the air supply tube 44 so that the tube 44 will not readily be disconnected from the air supply nipple 43.

An air pressure controller 46 is provided in an intermediate portion of the air supply tube 44 to control the pressure of air supplied. The air pressure controller 46 has a bleeder 47 which communicates with the air supply tube 44 and which opens upwardly to the atmosphere.

Figure 4:
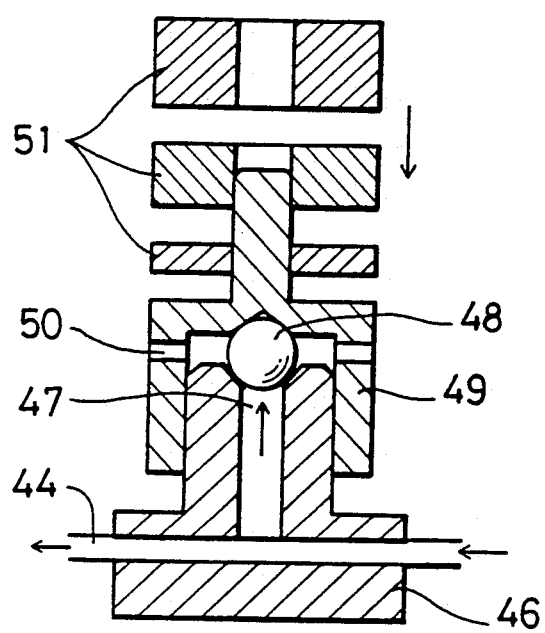
FIG. 4 is a fragmentary enlarged sectional view of an air pressure controller that is employed in the sheath device according to the present invention.
Figure 5A:
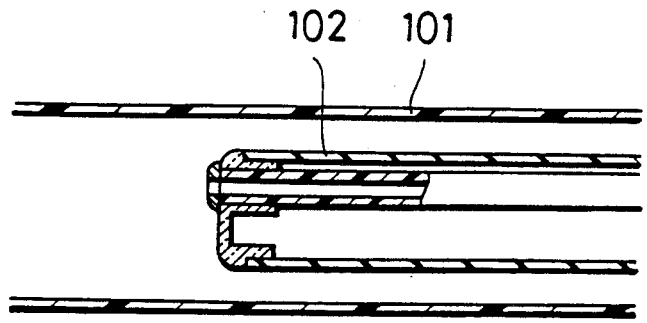
FIGS. 5A, 5B and 5C show the prior art.
Figure 5B:
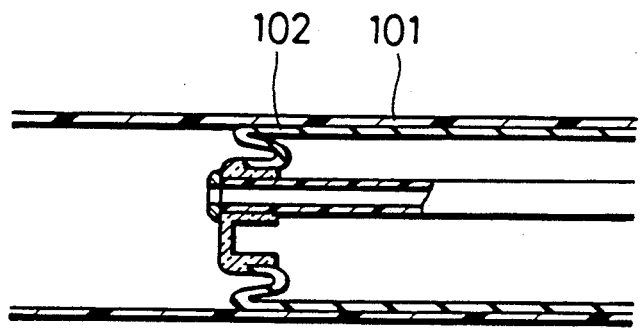
Figure 5C:
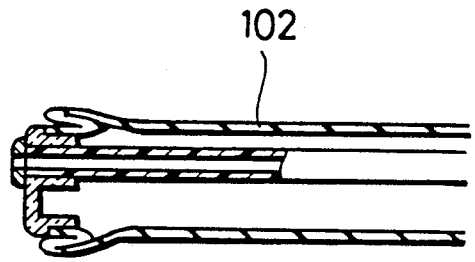

A ball valve 48 is placed on the upper end opening of the bleeder 47 from the upper side thereof to close the bleeder 47. As shown in FIG. 4, a weight 49 is placed on the upper side of the ball valve 48 to apply a load that resists the air pressure pushing the ball valve 48 upward. The weight 49 is provided with a bore 50 for releasing the air that flows out of the bleeder 47 when the ball valve 48 is caused to float up by the pressure of air supplied.

Reference numeral 51 denotes additional weights that are placed on the weight 49 when the ball valve 48 needs to be further weighed down. The additional weights 51 include a plurality of weights which have different weight, so that the load on the ball valve 48 can be changed incrementally by replacing an additional weight 51 with another or combining together a plurality of additional weights 51. It should be noted that the load that resists the air pressure within the supply tube 44 may be changed by replacing the ball valve 48 with another ball valve which has a different weight.

The operation of the above-described embodiment will now be explained.

First, the sheath 2 is inserted into the sheath cover 4, as shown by an arrow a in FIG. 2, to surround the tubular portion 21 of the sheath 2 with the tubular sheath cover member 41, as shown in FIG. 1. At this time, the mouth portion 24 is fitted into the sheath cover support member 42, so that the air supply opening 33 and the air supply nipple 43 communicate with each other.

The air supply tube 44 is connected to the air supply nipple 43. Then, the air supply pump 70 is activated to supply air into the sheath 2, and while doing so, only the distal end portion of the insert tube 1 (FIG. 1) of the endoscope is inserted into the sheath 2 from the proximal end thereof, as shown by an arrow b in FIG. 2. In consequence, the area between the packing 31 (FIG. 1) and the outer periphery of the insert tube 1 (FIG. 2) is hermetically sealed, and the tubular portion 21 begins to inflate. At this time, the distal end portion of the tubular portion 21 abuts against the tapered portion of the tubular sheath cover member 41, so that the longitudinal expansion of the tubular portion 21 is successively suppressed. Thus, no portion of the tubular portion 21 will expand in the longitudinal direction.

Figure 3:
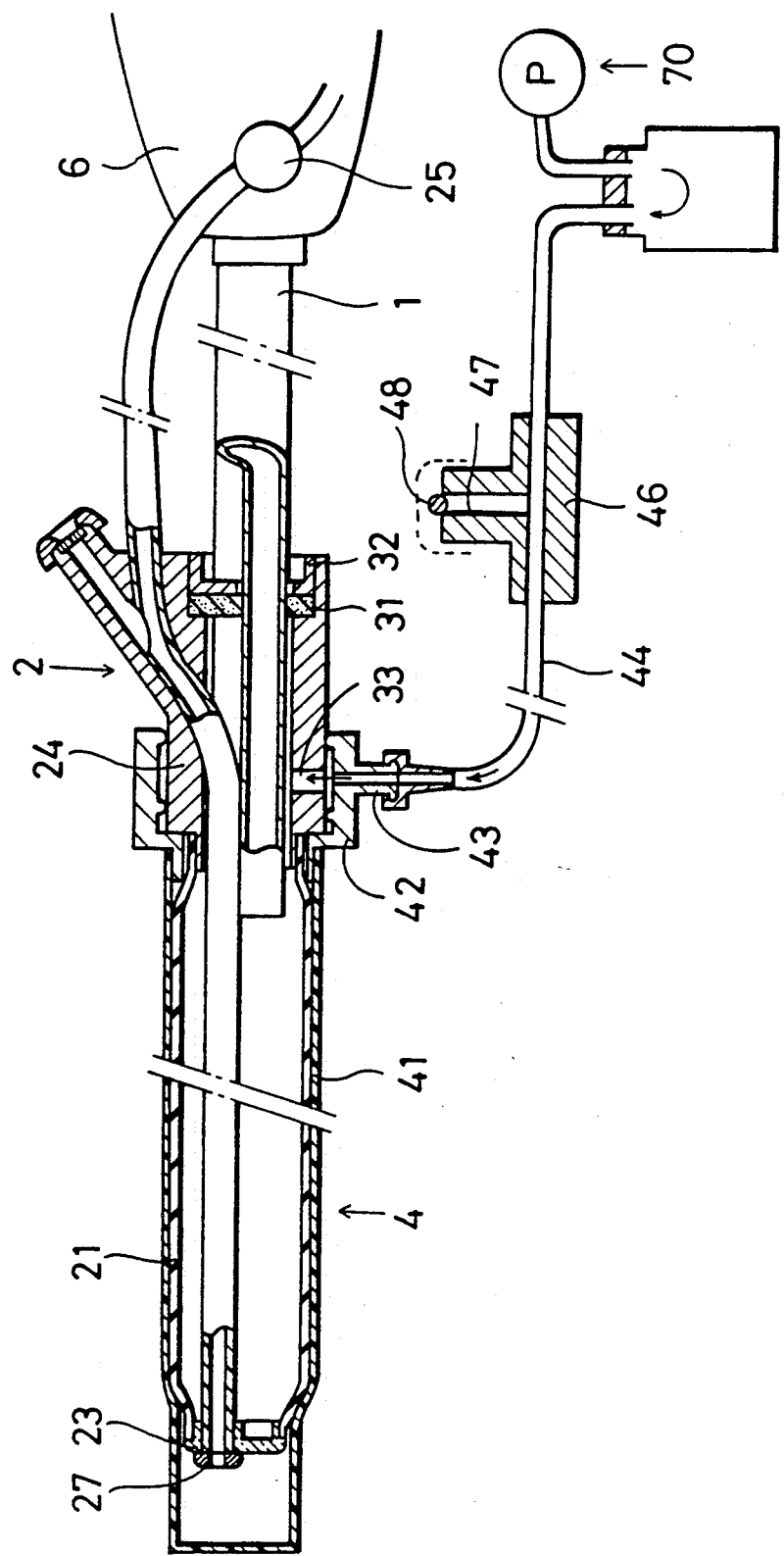
FIG. 3 is a sectional side view of the sheath device for an endoscope according to the present invention.

When the tubular portion 21 has inflated to such an extent that it abuts against the inner peripheral surface of the tubular sheath cover member 41, the insert tube 1 of the endoscope is inserted toward the distal end portion 23 of the sheath 2, as shown in FIG. 3. When the distal end of the insert tube 1 reaches the distal end portion 23 of the sheath 2, the air supply pump 70 is suspended to stop the supply of air. After the sheath 2 has completely deflated and come into close contact with the insert tube 1, the sheath cover 4 is removed from the sheath 2. At this time, the air supply tube 44, which is connected to the air supply nipple 43, is left connected to the sheath cover 4 and therefore removed from the sheath 2, together with the sheath cover 4.

After the completion of an endoscopic procedure, the sheath cover 4 is attached to the sheath 2, and the sheath 2 is inflated by sending air thereinto. Then, the insert tube 1 of the endoscope is removed from the sheath 2. At this time, the air supply tube 44 need not be connected to the air supply nipple 43 because the former has been in connection to the latter since the insertion of the insert tube 1 into the sheath 2.

In the air pressure controller 46, when the pressure of air supplied exceeds the load on the ball valve 48, the ball valve 48 floats up to open the bleeder 47, thereby releasing the air to the outside. Accordingly, the pressure of air supplied is maintained at a constant level that is determined by the load applied. When, for example, the type of sheath 2 used is changed, the pressure of air supplied can be adjusted to an optimal level by replacing one or more additional weights 51 with one or more others that have different weights.

It should be noted that, the higher the pressure of air supplied, the more easily the tubular portion 21 bursts, and when the tubular portion 21 bursts at a higher air pressure, the danger of scattering of pathogens increases correspondingly; therefore, the pressure of air supplied should be set at the lowest level with which the tubular portion 21 can be inflated.

When a diaphragm pump is employed as the air supply pump 70, the air that is supplied from the pump pulsates. Therefore, a device that absorbs the pulsation should be additionally provided in the air supply tube 44 between the air pressure controller 46 and the air supply pump 70.

Although in the foregoing embodiment the distal end of the tubular sheath cover member 41 is sealed to prevent leakage of filth, such as mucus or mucous membrane, attached to the sheath 2 after use, the distal end of the sheath cover member 4 may be open in a case where there is a weak possibility of contamination, or there is another proper contamination preventing means.

Although in the foregoing embodiment the air supply nipple 43 is provided on the sheath cover support member 42, the position of the nipple 43 is not necessarily limited thereto. For example, the nipple 43 may be provided on the mouth portion 24 of the sheath 2.

According to the present invention, the sheath cover is formed with a tapered portion to control the longitudinal expansion of the sheath when inflated. Since the sheath inflates into a favorable shape in conformity to the configuration of the sheath cover, the insert tube of the endoscope can be smoothly inserted into the sheath as far as the distal end thereof.

Since the pressure of air supplied can be digitally controlled by an air pressure controller having a simple structure, the control of the air pressure is easy and it is possible to readily prevent oversupply of air in regard to various types of sheaths employed. This is extremely useful for actual clinical procedures.

Thus, the sheath device for an endoscope according to the present invention enables the insert tube of the endoscope to be inserted into and removed from the sheath in favorable conditions without the fear that the sheath may be abnormally deformed or burst due to the oversupply of air.

In addition, according to the present invention, the air supply tube for supplying air into the sheath can be connected to the sheath cover. Accordingly, once it is attached to the sheath cover, the air supply tube need not be removed therefrom during an endoscopic procedure, that is, from the time when the insert tube of the endoscope is inserted into the sheath until the procedure is completed. Thus, the sheath device of the present invention is very easy to handle and displays superior operability.

While the invention has been described by reference to a specific embodiment chosen for purposes of illustration, it should be apparent that numerous modifications could be made thereto by those skilled in the art without departing from the basic concept and scope of the invention.

We claim:
1. A sheath device for an endoscope comprising:
a sheath which is inflatable with a gas that is sent into the inside thereof to cover an insert tube of said endoscope; and
a sheath cover which is formed in the shape of a tube that surrounds said sheath with a space left therebetween to control overinflation of said sheath, a portion of said sheath cover that surrounds the distal end portion of said sheath being tapered toward the distal end of said sheath cover.
2. A sheath device for an endoscope according to claim 1, wherein said sheath has a tubular portion which is formed in the shape of a thin-walled cylinder using an elastic material.

3. A sheath device for an endoscope according to claim 2, wherein said sheath has a distal end portion which is formed from a non-elastic, transparent material and which is rigidly secured to the distal end of said tubular portion.

4. A sheath device for an endoscope according to claim 3, wherein said tubular portion has a mouth portion which is connected to the proximal end thereof, said mouth portion being provided with a packing for hermetically sealing the outer periphery of said insert tube of said endoscope when inserted, without any gap therebetween.

5. A sheath device for an endoscope according to claim 4, further comprising a gas supply opening which is provided in said mouth portion to supply a gas into said sheath.

6. A sheath device for an endoscope according to claim 1, wherein said sheath cover is formed in the shape of a tube the distal end of which is sealed.

7. A sheath device for an endoscope according to claim 2, wherein a relatively short portion of said sheath cover, which is closer to the distal end than said tapered portion, has such an inner diameter that said sheath is loosely fitted therein, whereas a relatively long portion of said sheath cover, which is closer to the proximal end than said tapered portion, has an inner diameter that is smaller than a critical diameter at which said sheath bursts from overinflation.

8. A sheath device for an endoscope comprising:
a sheath which is inflatable with a gas that is sent into the inside thereof to cover an insert tube of said endoscope;
a gas supply means for supplying a gas into said sheath to inflate it; and
a gas pressure control means for adjusting a pressure of said gas supplied by said supplying means at a predetermined level.

9. A sheath device for an endoscope according to claim 8, wherein said gas supply means has a gas supply passage, and said gas control means has a bleeder which communicates with said gas supply passage and opens upwardly to the atmosphere, and a ball valve which is provided on the upper side of said bleeder.

10. A sheath device for an endoscope according to claim 9, wherein said ball valve is interchangeable.

11. A sheath device for an endoscope according to claim 9, further comprising an interchangeable weight which is used to weigh down said ball valve.

12. A sheath device for an endoscope comprising:
a sheath which is inflatable with a gas that is sent into the inside thereof to cover an insert tube of said endoscope;
a sheath cover which is detachably provided with respect to said sheath to control overinflation of said sheath, said sheath cover surrounding said sheath with a space left therebetween; and
a gas supply tube connecting means which is provided on said sheath cover to connect a gas supply tube for supplying a gas into said sheath.

13. A sheath device comprising:
a sheath which is inflatable with a gas that is sent into the inside thereof to cover an object; and
a sheath cover which is formed in the shape of a tube that surrounds said sheath with a space left therebetween to control overinflation of said sheath, a portion of said sheath cover that surrounds the distal end portion of said sheath being tapered toward the distal end of said sheath cover.

* * * * *